United States Patent
Khopade et al.

(10) Patent No.: US 11,000,475 B2
(45) Date of Patent: May 11, 2021

(54) OPHTHALMIC SOLUTION OF DIFLUPREDNATE

(71) Applicant: Sun Pharma Advanced Research Company Limited, Mumbai (IN)

(72) Inventors: Ajay Jaysingh Khopade, Baroda (IN); Arindam Halder, Baroda (IN); Ankit Shaileshkumar Shah, Baroda (IN)

(73) Assignee: Sun Pharma Advanced Research Company Limited, Mumbai (IN)

( * ) Notice: Subject to any disclaimer, the term of this patent is extended or adjusted under 35 U.S.C. 154(b) by 0 days.

(21) Appl. No.: 15/768,285

(22) PCT Filed: Oct. 15, 2016

(86) PCT No.: PCT/IN2016/050351
§ 371 (c)(1),
(2) Date: Apr. 13, 2018

(87) PCT Pub. No.: WO2017/064731
PCT Pub. Date: Apr. 20, 2017

(65) Prior Publication Data
US 2018/0296571 A1    Oct. 18, 2018

(30) Foreign Application Priority Data

Oct. 16, 2015  (IN) .......................... 3932/MUM/2015
Jul. 22, 2016  (IN) ............................. 201621025198

(51) Int. Cl.
| | |
|---|---|
| *A61K 9/08* | (2006.01) |
| *A61K 9/00* | (2006.01) |
| *A61K 31/573* | (2006.01) |
| *A61P 27/04* | (2006.01) |
| *A61K 47/02* | (2006.01) |
| *A61K 47/18* | (2017.01) |
| *A61K 47/32* | (2006.01) |
| *A61P 27/02* | (2006.01) |
| *A61K 47/44* | (2017.01) |

(52) U.S. Cl.
CPC .............. *A61K 9/08* (2013.01); *A61K 9/0048* (2013.01); *A61K 31/573* (2013.01); *A61K 47/02* (2013.01); *A61K 47/186* (2013.01); *A61K 47/32* (2013.01); *A61K 47/44* (2013.01); *A61P 27/02* (2018.01); *A61P 27/04* (2018.01)

(58) Field of Classification Search
CPC combination set(s) only.
See application file for complete search history.

(56) References Cited

U.S. PATENT DOCUMENTS

| 5,520,920 A | 5/1996 | Castillo et al. |
| 5,556,848 A | 9/1996 | Kimura et al. |
| 6,114,319 A | 9/2000 | Kimura et al. |
| 2008/0194532 A1 | 8/2008 | Rabinovich-Guilatt et al. |
| 2009/0169629 A1 | 7/2009 | Lambert et al. |
| 2012/0083534 A1* | 4/2012 | Smith ................. A61K 9/0048 514/635 |
| 2014/0378401 A1 | 12/2014 | Horn |
| 2015/0190407 A1 | 7/2015 | Hosseini et al. |

FOREIGN PATENT DOCUMENTS

| EP | 0659433 | 6/1995 |
| WO | WO1998057646 | 12/1998 |
| WO | WO 2016/123079 A1 | 8/2016 |

OTHER PUBLICATIONS

Moroi Y. (1992) Mixed Micelle Formation. In: Micelles. Springer, Boston, MA (Year: 1992).*
International Search Report from International Application No. PCT/IN2016/050351 dated Jan. 27, 2017.
Suresh PK et al., "Patent perspectives for corticosteroids based ophthalmic therapeutics", 2014, Recent Pat Drug Deliv Formul; 8(3):206-23. Abstract Only.
Sah AK et al., "Recent Advances in Ocular Drug Delivery, with Special Emphasis on Lipid Based Nanocarriers", 2015, Recent Pat Nanotechnol.; 9(2):94-105. Abstract Only.
Henderson BA et al., "Safety and efficacy of bromfenac ophthalmic solution (Bromday) dosed once daily for postoperative ocular inflammation and pain", Nov. 2011, Ophthalmology ;118 (11):2120-7. Doi: 10.1016/j.ophtha.2011.04.035. Epub Jul. 16, 2011. Abstract Only.
Sharel C et al., "Retrospective Analysis of Patients on Difluprednate for Treatment of Refractory Intraocular Inflammation", Apr. 2011, ARVO Annual Meeting Abstract, Investigative Ophthalmology & Visual Scienc, vol. 52, 4320.
Daniel Feiler et al, "Resolution of uveitic cystoid macular edema with topical difluprednate", Jun. 2015, ARVO Annual Meeting Abstract, Investigative Ophthalmology & Visual Science, vol. 56, 6175.
A. Okumura et al.,"Efficacy of Difluprednate Ophthalmic Emulsion in Preclinical Studies of Uveitis", May 2007, ARVO Annual Meeting Abstract, Investigative Ophthalmology & Visual Science, vol. 48, 2652.

(Continued)

*Primary Examiner* — Hasan S Ahmed
(74) *Attorney, Agent, or Firm* — Medler Ferro Woodhouse & Mills PLLC

(57) ABSTRACT

The present invention provides an ophthalmic solution comprising a. therapeutically effective concentration of difluprednate, a crystal growth inhibitor and pharmaceutically acceptable amounts of a solubilizer comprising a mixture of i. quaternary ammonium compound and ii. polyethoxylated castor oil, b. in an aqueous vehicle. wherein the crystal growth inhibitor is polyvinyl alcohol or its derivatives. Also, the present invention provides a method of treatment of inflammatory disorder of the eye, said method comprising administering into the eye of a person in need thereof, an aqueous solution comprising difluprednate as the sole active ingredient at a concentration of 0.02% to 0.04% weight by volume in an aqueous vehicle, wherein the solution is free of oil and wherein the solution is administered twice-a-day.

15 Claims, No Drawings

(56) References Cited

OTHER PUBLICATIONS

M. Mochizuki et al.,"A Phase III, Open-Label, Clinical Study of Difluprednate Ophthalmic Emulsion (DFBA), 0.05% in the Treatment of Severe Refractory Anterior Uveitis", May 2007, ARVO Annual Meeting Abstract, Investigative Ophthalmology & Visual Science, vol. 48, 3905.

Foster CS et al., "Efficacy and safety of rimexolone 1% ophthalmic suspension vs 1% prednisolone acetate in the treatment of uveitis", Aug. 1996, Am J Ophthalmol.; 122 (2):17182; Abstract Only.

John D. Sheppard et al., "Difluprednate 0.05% Versus Prednisolone Acetate 1% for Endogenous Anterior Uveitis: A Phase III, Multicentre, Randomized Study",Departments of Ophthalmology, Microbiology, and Molecular Biology, Eastern Virginia Medical School, Norfolk, Virginia, United States, IOVS May 2014 vol. 55 No. 5, 2993-3002.

S. Ohno et al., "A Phase III, Non-Inferiority Study of Difluprednate Ophthalmic Emulsion (DFBA), 0.05% in the Treatment of Anterior Uveitis", May 2007, ARVO Annual Meeting Abstract, Investigative Ophthalmology & Visual Science May 2007, vol. 48, 3904.

Hideyasu Yamauchi et al., "Ocular anti-inflammatory and systemic immunosuppressive effects of topically applied flurometholone", Research Laboratory, Santen Pharmaceutical Co., Ltd., Higashiyodogawa-ku, Osaka 533 and *Department of Pharmacology, Faculty of Pharmaceutical Sciences, Osaka University, Suita, Osaka 565, Japan Accepted Jul. 30, 1978.

Donnenfeld E, "Difluprednate for the prevention of ocular inflammation postsurgery: an update" Clinical Ophthalmology 2011, vol. 5, page No. 811-816 (Year:2011).

Non-final Office Action issued in U.S. Appl. No. 15/768,316, dated Jan. 25, 2019.

Final Office Action issued in U.S. Appl. No. 15/768,316, dated Sep. 9, 2019.

Non-final Office Action issued in U.S. Appl. No. 15/768,316, dated Jul. 24, 2020.

* cited by examiner

OPHTHALMIC SOLUTION OF DIFLUPREDNATE

FIELD OF THE INVENTION

The present invention relates to an ophthalmic aqueous solution of difluprednate or its pharmaceutically acceptable salt and its use in the treatment of inflammatory disorder of the eye.

The present invention relates to a method of treating inflammatory disorder of the eye, said method comprising administering into the eye of a patient in need thereof, an ophthalmic aqueous solution of difluprednate.

BACKGROUND OF THE INVENTION

Difluprednate is an anti-inflammatory corticosteroid drug represented by formula I below.

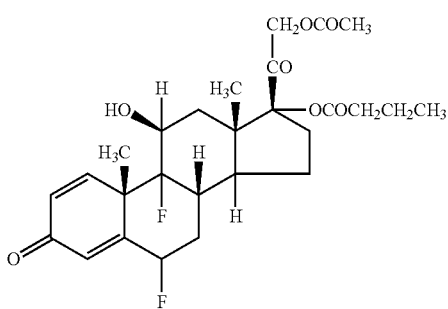

Formula I

Difluprednate, a steroidal drug is practically insoluble in aqueous vehicle. The currently marketed formulation of difluprednate is an emulsion dosage form of difluprednate, approved and marketed in the United States under the brand name of DUREZOL®. Durezol® is an ophthalmic emulsion formulation of difluprednate which comprises 0.05% w/v difluprednate emulsified between castor oil and water. It is not a clear aqueous solution. The U.S. Pat. No. 6,114,319 (herein after referred to as the '319 patent) is listed in the "Orange Book: Approved Drug Products with Therapeutic Equivalence Evaluations" against Durezol® product and describes an emulsion formulation of difluprednate which contains an oil and an emulsifier. Durezol® emulsion formulation is indicated for the treatment of inflammation and pain associated with ocular surgery and endogenous anterior uveitis when administered four times a day. As the emulsion needs to be instilled four times-a-day, there are high chances of patient non-compliance and missing a dose. The prior art formulations of difluprednate does not provide prolonged action. Further, it has been reported and also noted in the approved label of Durezol® that the most common adverse reactions in subjects exposed to Durezol®, (occurring in 5-10% of subjects), include blurred vision, eye irritation, eye pain, headache, increased TOP, iritis, limbal and conjunctival hyperemia, punctate keratitis. Thus, there lies a need for a formulation of difluprednate that is devoid of these side effects and which overcomes the existing drawbacks.

SUMMARY OF THE INVENTION

The present invention provides an aqueous solution comprising
a. therapeutically effective concentration of difluprednate, a crystal growth inhibitor and pharmaceutically acceptable amounts of a solubilizer comprising a mixture of
  i. quaternary ammonium compound and
  ii. polyethoxylated castor oil,
b. in an aqueous vehicle.
wherein the crystal growth inhibitor is polyvinyl alcohol or its derivatives.

The present invention in another aspect, provides a method of treating inflammatory disorder of the eye, said method comprising administering into the eye of a person in need thereof, an aqueous solution comprising difluprednate as the sole active ingredient at a concentration of about 0.02% to 0.04% weight by volume, wherein the solution is free of oil and wherein the solution is administered twice-a-day.

DETAILED DESCRIPTION OF THE INVENTION

These "aqueous solution" as stated herein, is a solution of difluprednate in aqueous vehicle, wherein difluprednate is in the solubilized form and not in particulate form, either microparticulate or nanoparticulate or in micellar form.

The term 'crystal growth inhibitor' as used herein means the additional excipients that prevent the difluprednate from being precipitated or crystallized out from the aqueous vehicle. The screening for inhibitory effect of crystal growth of difluprednate may be carried out by physical observation as well as by determining the clarity of the aqueous solution, immediately upon formulating or on storage. The solutions show percentage transmission greater than 90%, more preferably greater than 95%. When light is allowed to pass through the ophthalmic solution, the percentage of incident light which is transmitted through the solution is referred to as "percent transmission". Generally, the percentage transmission is determined at a wavelength of about 650 nm, but any other suitable wavelength may be selected for determining the clarity of the solution. The aqueous solution of the present invention show percent transmission greater than 90%, more preferably greater than 95%, more preferably greater than 99%. The aqueous solution remains clear and free from particles, crystals or precipitate, upon long term storage at temperatures between 2° C. to 30° C. for a period of 6 months or more.

The aqueous solution of the present invention is free of oil. The term 'oil' as used herein refers to oils which are hydrophobic compounds. The examples of the 'oil' include, but are not limited to triglycerides such as, castor oil, peanut oil, arachis oil, mineral oil and the like. The term 'oil' does not include amphiphilic compounds or surfactants obtained by derivatising oil with a hydrophilic entity such as for example polyethoxylated castor oil.

The ophthalmic aqueous solution of the present invention comprises
a. therapeutically effective concentration of difluprednate, a crystal growth inhibitor and pharmaceutically acceptable amounts of a solubilizer comprising a mixture of
  i. quaternary ammonium compound and
  ii. polyethoxylated castor oil,
b. in an aqueous vehicle.
wherein the crystal growth inhibitor is polyvinyl alcohol or its derivatives.

The ophthalmic aqueous solution used according to the present invention comprises difluprednate as the sole therapeutically active ingredient. The word 'difluprednate' as used herein includes prodrugs of difluprednate wherein the hydroxyl group in difluprednate is converted to a labile ester or an amide. In one embodiment, the ophthalmic aqueous solution according to the present invention does not include povidone-iodine or any other active ingredient and is always the sole active ingredient. The concentration (% weight by volume) of difluprednate is expressed in terms of difluprednate base. It is present at a concentration that ranges from about 0.005% to 0.07% weight by volume, preferably from about 0.02% to 0.045% weight by volume, such as for example 0.025, 0.03, 0.035, 0.036, 0.037, 0.038, 0.039 or 0.04%, 0.041%, 0.042%, 0.043% weight by volume, more preferably from about 0.02% to 0.04% weight by volume.

The ophthalmic aqueous solution according to the present invention comprises solubilizer which is a mixture of quaternary ammonium compound and polyethoxylated castor oil. It was found that when individual solubilizer i.e. quaternary ammonium compound alone or polyethoxylated castor oil alone were used, the attempts to solubilize difluprednate were not successful and difluprednate precipitated from the solution, either immediately or upon storage. Surprisingly, when the mixture of these two category of solubilizers is used, clear aqueous solution was obtained i.e. there was no precipitation of difluprednate upon preparation or on storage.

The quaternary ammonium compound is selected from, but not limited to, benzalkonium chloride, myristyl gamma picolinium chloride, benzethonium chloride, benzododecinium bromide, cetalkonium chloride, cetylpyridinium chloride, cetrimonium, tetraethylammonium bromide, polyhexamethylene biguanide, oleyl amine and the like. In some preferred embodiments, the quaternary ammonium compound is selected from benzalkonium chloride and myristyl gamma picolinium chloride. The quaternary ammonium compound is used in the ophthalmic solution in amounts ranging from about 0.0002% to 0.1% weight by volume, preferably from about 0.002% to about 0.08% weight by volume, such as for example 0.003, 0.004, 0.005, 0.006, 0.007, 0.008, 0.009, 0.01, 0.02, 0.03, 0.04, 0.05, 0.06 or 0.07% weight by volume. According to one particular preferred embodiment, the quaternary ammonium compound is benzalkonium chloride and is present in the ophthalmic aqueous solution in an amount ranging from about 0.0002% to 0.08% weight by volume, preferably from about 0.0002% to 0.05% weight by volume, more preferably from about 0.005% to 0.05% weight by volume, more preferably from about 0.01% to 0.05% weight by volume. The polyethoxylated castor oil that is used as a solubilizer according to the present invention is also known by other terms like polyoxyl castor oil, or polyoxyethylene castor oil. It is marketed under various tradenames such as Cremophor®, Acconon®, Arlatone®, Eumulgin®, Etocas®, Jeechem®, Hetoxide®, Nikkol®, Croduret®. The polyethoxylated castor oils or polyoxyethylene castor oil derivatives that may be used in the ophthalmic aqueous solutions of the present invention are described in "Handbook of Pharmaceutical Excipients", fifth edition, 2006, page 572-578. The ophthalmic aqueous solution of the present invention preferably comprises polyoxyl 35 castor oil, marketed under the tradename Cremophor® EL by BASF Corp.; polyoxyl 40 castor oil marketed under the tradename Croduret®40 or Etocas®40, polyoxyl 60 castor oil marketed under the tradename Jeechem® CA-60; polyoxyl 15 castor oil marketed under the tradename Jeechem® CA-15 or Acconon®CA-15. The polyethoxylated castor oils are used in the ophthalmic aqueous solution of the present invention in pharmaceutically acceptable amounts. The pharmaceutically acceptable amount of 'polyethoxylated castor oil' ranges from about 1.0% to 10.0% weight by volume. Preferably, the polyethoxylated castor oil is present in the ophthalmic aqueous solution in an amount ranging from about 1.5% to 6.0% w/v, such as for example 2.0, 2.5, 3.0, 3.5, 4.0, 4.5, 5.0, or 5.5% weight by volume of the solution. According to one particular preferred embodiment, the 'polyethoxylated castor oil' is polyoxyl 35 castor oil and is present in the ophthalmic aqueous solution in pharmaceutically acceptable amount ranging from about 3.0% to 5.0% w/v. In one particularly preferred embodiment, the aqueous solution comprises a mixture of benzalkonium chloride and polyoxyl 35 castor oil as the solubilizer.

The crystal growth inhibitor present in the aqueous solution is polyvinyl alcohol or its derivatives. Without the presence of these crystal growth inhibitors, difluprednate does not remain in solubilized form in aqueous vehicle and precipitates out upon standing/storage.

The derivatives of the polyvinyl alcohol include, but are not limited to, polyvinyl alcohol-polyethylene glycol graft copolymer (marketed under the trade name Kollicoat®), poly (vinyl alcohol co ethylene), polystyrene-polyvinyl alcohol graft co-polymer, polyvinyl alcohol-polyvinylpyrrolidone graft co-polymer, polyvinyl alcohol-lactic acid graft co-polymer, polyvinyl alcohol-carregeenan-graft co-polymer, polyvinyl alcohol-polyether graft copolymer and the like and mixtures thereof. In one specific embodiment, the crystal growth inhibitor is polyvinyl alcohol. It ranges from about 0.1% to 5.0% weight by volume, preferably from about 0.5% to 3.0%, such as for example 0.6, 0.7, 0.8 0.9, 1.0, 1.1, 1.2, 1.3, 1.4, 1.5, 1.6, 1.7, 1.8, 1.9, 2.0, 2.2, 2.4, 2.5, 2.6, 2.7, 2.8 or 2.9% weight by volume of the solution.

The aqueous solution of the present invention may further include, other conventional excipients such as viscosity increasing agent, preservatives, chelating agents, cosolvents, buffers and so on.

The viscosity increasing agent that can be used include, but are not limited to, carboxymethylcellulose, hydroxypropyl methylcellulose, hydroxyethyl cellulose, hydroxypropyl cellulose, methylcellulose, hydroxyethyl starch, dextran, xanthan gum, sodium alginate, starch, sodium hyaluronate, carbopols, polyvinyl pyrrolidone and the like or mixtures thereof. In one preferred embodiment, viscosity enhancer is carboxymethylcellulose. Suitably, in preferred embodiments, the aqueous solution does not contain viscosity enhancer's such as polycarbophil and chitosan which have high molecular weight. The viscosity of the aqueous solution according to the present invention generally ranges from about 1 cps to 2000 cps, preferably about 2 cps to 1000 cps, more preferably about 1 cps to 300 cps, more preferably from about 2 cps to 200 cps. In particularly preferred embodiments, the viscosity of the ophthalmic aqueous solution is between about 2 cps to 30 cps. In one embodiment, the present invention provides an ophthalmic aqueous solution comprising a therapeutically effective amount of difluprednate as the sole active ingredient and having a viscosity from 2 cps to 200 cps, wherein the solution is effective in treating inflammatory disorder of the eye when administered twice-a-day.

The ophthalmic aqueous solution may further contain one or preservative, particularly when the dosage form is multiple dose and not single dose. The preservatives that may be used include, but are not limited to, benzyl alcohol, cetrimide, chlorhexidine, chlorobutanol, mercurial preservatives like phenylmercuric nitrate, phenylmercuric acetate, thimerosal, phenylethyl alcohol, Polyquad®, stabilized oxy-chlorocomplex, stabilized peroxides and perborates and the like. It is also possible to include safer preservative systems and preservative efficacy enhancers such as edetate disodium, N-lauroyl sarcosine or its sodium salt, boric acid, borates, biguanides like polyhexamethylene biguanide, polyoxyalkylene diamine biguanide or its water-soluble salt; 1,1'-hexamethylene-bis-{5-(4-chlorophenyl)-biguanide}; 1,1'-hexamethylene-bis-{5-(4-fluorophenyl)-biguanide}; (N,N"-bis(2-ethyl hexyl)-3,12-diimino-2,4,11,13-tetraazatetra decanediimidamine; parabens (such as methyl-propyl, isopropyl and butyl-paraben), pyruvates, stabilized oxychloro compounds, sorbic acid/potassium sorbate, metal ions, peroxides, amino acids such as arginine, tromethamine and mixtures thereof. According to another embodiment of the present invention, the ophthalmic aqueous solution may be self preserving.

In one preferred embodiment, the ophthalmic aqueous solution uses a preservative selected from a biguanide, boric acid, N-lauroyl sarcosine or mixtures thereof. In one preferred embodiment, the ophthalmic aqueous solution comprises polyhexamethylene biguanide in an amount ranging from about 0.001% to 0.04% w/v, preferably from about 0.002% to 0.02% w/v, such as for example 0.003, 0.004, 0.005, 0.006, 0.007, 0.008, 0.009, 0.01 or 0.02% w/v. In one preferred embodiment, the ophthalmic aqueous solution comprises boric acid in an amount ranging from about 0.05% to 1.5% w/v, preferably from about 0.1% to 1.0% w/v, such as for example, 0.2, 0.3, 0.4, 0.5, 0.6, 0.7, 0.8 or 0.9% w/v, more preferably from 0.4% to 0.7% w/v. In one preferred embodiment, the ophthalmic aqueous solution comprises N-lauroyl sarcosine in an amount ranging from about 0.001 to 0.5% w/v, such as for example 0.002, 0.003, 0.004, 0.005, 0.006, 0.007, 0.008, 0.009, 0.01, 0.02, 0.03, 0.04, 0.05, 0.06, 0.07, 0.08, 009, 0.1, 0.15, 0.2, 0.25, 0.3, 0.35, 0.4 or 0.45% w/v, preferably from about 0.01 to 0.1% w/v, more preferably from 0.02 to 0.05% w/v. In one particularly preferred embodiment, the ophthalmic aqueous solution comprises a mixture of polyhexamethylene biguanide, boric acid and N-lauroyl sarcosine as preservative. In one specific embodiment, it was found that when benzalkonium chloride was used alone, the solution was not preserved effectively, which was indicated by the results of the preservative efficacy test. When a biguanide was added to the solution, the solution was found to be preserved effectively i.e. the solution passed the preservative efficacy test as specified in European Pharmacopoeia.

The chelating agents that can be used include, but are not limited to, edetate disodium, ethylenediamine tetracetic acid, edetic acid, disodium edetate dihydrate, diethylenetriamine pentaacetic acid etc. A preferred chelating agent is ethylenediamine tertaacetic acid or disodium edetate. In one preferred embodiment, the ophthalmic aqueous solution comprises disodium edetate in an amount ranging from about 0.001% to 0.5% w/v, such as for example 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4 or 0.45% w/v, preferably from about 0.01 to 0.1% w/v, more preferably in an amount of 0.03-0.07% w/v.

The pH adjusting agents and/or buffer that may be used are selected from, but not limited to, acetic acid, sodium acetate, tartaric acid, sodium tartrate, citric acid, sodium citrate, hydrochloric acid, sodium hydroxide or mixtures thereof. The osmotic/tonicity adjusting agents that may be used include, but are not limited to, sodium chloride, potassium chloride, sodium bromide, calcium chloride, mannitol, glycerol, sorbitol, propylene glycol, dextrose, sucrose, mannose and the like and mixtures thereof. These solutions are characterized by osmolalities of 250-375 mOsm/kg, preferably 270-350 mOsm/kg, such as for example 275, 280, 285, 290, 295, 300, 305, 310, 315, 320, 325, 330, 335, 340 or 345 mOsm/kg. Osmolality of the solutions is adjusted by addition of an osmotic/tonicity adjusting agent.

The co-solvents that can be used, include, but are not limited to, glycerol or glycerine, propylene glycol, ethylene glycol, polyethylene glycol, glycofurol and like. Glycerol may be present in the ophthalmic aqueous solution of the present invention in an amount ranging from about 0.5% w/v to about 5.0% w/v, such as for example 1.0, 1.5, 2.0, 2.5, 3.0, 3.5, 4.0, or 4.5% w/v, preferably from about 1.0% w/v to about 3.0% w/v of the solution.

A representative aqueous solution of the present invention comprises or consists essentially of, or consists of the following composition:

| Ingredient/function | Range % weight by volume |
|---|---|
| Active drug- Difluprednate | 0.02-0.04 |
| A quarternary ammonium compound (as solubilizer 1) | 0.0002-0.08 |
| Polyethoxylated castor oil (as solubilizer 2) | 1.5-6.0 |
| Polyvinyl alcohol or its derivative as a Crystal growth Inhibitor | 0.1-5.0 |
| Aqueous Vehicle | q.s to 100 |

According to various aspects, the ophthalmic aqueous solution according to the present invention comprises or consists essentially of, or consists of the following composition:

| Ingredients | Range % weight by volume |
|---|---|
| Difluprednate | 0.02-0.04 |
| A quarternary ammonium compound (as solubilizer 1) | 0.0002-0.08 |
| Polyethoxylated castor oil (Polyoxyl 35 castor oil) | 1.5-6.0 |
| Polyvinyl alcohol or its derivative as a Crystal growth Inhibitor | 0.1-5.0 |
| Cosolvent | 0.5-5.0 |
| Aqueous Vehicle for eg. Water for injection | q.s to 100 |

According to various aspects, the ophthalmic aqueous solution according to the present invention comprises or consists essentially of, or consists of the following composition:

| Ingredients | Range % weight by volume |
|---|---|
| Difluprednate | 0.02-0.04 |
| Quaternary ammonium compound | 0.0002-0.08 |
| Polyethoxylated castor oil | 1.5-6.0 |
| Polyvinyl alcohol or its derivative as a Crystal growth Inhibitor | 0.1-5.0 |
| Co-solvent | 0.5-5.0 |
| n-lauroyl sarcosine | 0.01-0.1 |
| Poly hexa methylene biguanide | 0.001-0.04 |
| Other Preservative | 0.1-1.0 |
| Chelating agent | 0.01-0.1 |
| Buffer | 0.001-0.05 |
| Water for Injection | q.s. to 100 |

According to various aspects, the ophthalmic aqueous solution according to the present invention comprises or consists essentially of, or consists of the following composition:

| Ingredients | Range % weight by volume |
| --- | --- |
| Difluprednate | 0.03-0.04 |
| Quaternary ammonium compound | 0.01-0.05 |
| Polyethoxylated castor oil | 3.0-5.0 |
| Crystal growth inhibitor, polyvinyl alcohol or its derivative | 0.5-3.0 |

A first ophthalmic aqueous solution, according to various aspects, comprises or consists essentially of, or consists of the following Composition:

| Ingredients | Range % weight by volume |
| --- | --- |
| Difluprednate | 0.03-0.04 |
| Quaternary ammonium compound | 0.025 |
| n-lauroyl sarcosine | 0.03 |
| Polyethoxylated castor oil | 5.00 |
| Polyvinyl alcohol or its derivative | 1.40 |
| Poly hexa methylene biguanide | 0.005 |
| Other conventional excipients | 0.05 to 2 |
| Aqueous Vehicle for eg. Water for injection | q.s to 100 |

A second ophthalmic aqueous solution, according to various aspects, comprises or consists essentially of, or consists of the following Composition:

| Ingredients | Range in (% w/v) |
| --- | --- |
| Difluprednate | 0.03 |
| Benzalkonium chloride | 0.02 |
| Polyoxyl 35 castor oil (Cremophor ® EL) | 4.0 |
| Polyvinyl alcohol or its derivative | 1.4 |
| Other conventional excipients | 0.05 to 2 |
| Aqueous Vehicle for eg. Water for injection | q.s to 100 |

The present invention in another aspect, provides a method of treatment of inflammatory disorder of the eye, said method comprising administering into the eye of a person in need thereof, an aqueous solution comprising difluprednate as the sole active ingredient at a concentration of 0.02% to 0.04% weight by volume in an aqueous vehicle, wherein the solution is free of oil and wherein the solution is administered twice-a-day.

The inflammatory disorder of the eye may be one or more of the pain and inflammation associated with ocular surgery and uveitis. In particular aspect, the present invention provides method of treating acute anterior uveitis or chronic uveitis, said method comprising twice-a-day administration into the eye of a person in need thereof, an aqueous solution comprising difluprednate as the sole active ingredient at a concentration of 0.02% to 0.04% weight by volume in an aqueous vehicle, wherein the solution is free of oil. Particularly, the present invention provides method of treating acute anterior uveitis or chronic uveitis, said method comprising twice-a-day administration into the eye of a person in need thereof, an aqueous solution comprising difluprednate as the sole active ingredient at a concentration of 0.04% weight by volume in an aqueous vehicle, wherein the solution is free of oil.

Generally, the anti-inflammatory effect of the solution can be determined by known techniques or animal models. The inventors found that the method of treating acute or chronic uveitis is effective when tested in animal models as well as in human patients.

It was surprisingly found that the anti-inflammatory effect achieved by twice-a-day administration of the aqueous solution having difluprednate at concentration of 0.03% and 0.04% weight by volume was equivalent to the anti-inflammatory action obtained by four-times-a-day administration of an emulsion formulation of the prior art, available under the trade name of Durezol® and having difluprednate at concentration of 0.05% w/v. This is indeed surprisingly and unexpected because the prior art composition includes significant amount of oil, moreover it contains 0.05% weight by volume of difluprednate and is instilled four time daily as compared to the aqueous solution of present invention having 0.04% w/v of difluprednate, and administered twice daily and wherein the ophthalmic aqueous solution is free of oil. This is all the more surprising because difluprednate being hydrophobic/oil soluble is considered to remain in the oil phase and thus, expected to provide better efficacy in an emulsion type of composition compared to a composition which is aqueous based and most importantly, free of oil. The results found by the inventors are in fact contrary to the established hypothesis.

In one preferred embodiment, the ophthalmic aqueous solution is useful for the treatment of uveitis and comprises difluprednate at a concentration ranging from about 0.02% weight by volume to 0.04% weight by volume. In one particularly preferred embodiment, the ophthalmic aqueous solution of the present invention comprises difluprednate at a concentration of 0.03% weight by volume. In another particularly preferred embodiment, the ophthalmic aqueous solution of the present invention comprises difluprednate at a concentration of 0.04% weight by volume.

In another aspect, the present invention provides a method of treating inflammatory disorder of the eye, said method comprising administering into the eye of a person in need thereof, an aqueous solution comprising difluprednate as the sole active ingredient at a concentration of about 0.02% to 0.04% weight by volume, wherein the solution is free of oil and wherein the solution is administered twice-a-day. In other words, the present invention provides an ophthalmic aqueous solution for use in treatment of inflammatory disorder of the eye, the aqueous solution comprising difluprednate as the sole active ingredient at a concentration of 0.02% to 0.04% weight by volume of the solution in an aqueous vehicle, the solution being free of oil, wherein the solution is effective in treating inflammatory disorder of the eye when administered twice-a-day.

The present invention provides a clear aqueous solution formulation of difluprednate for use in treatment of inflammatory disorder of the eye which can be administered twice-a-day with added advantage that the solution form enables to use lower concentration of difluprednate as compared to the existing prior art compositions or marketed products.

The present invention provides a remarkable improvement in the method of treatment of inflammatory disorder of the eye. By virtue of clear nature of the aqueous solution being free of any suspended particles, reduced frequency of administration and potential for use of reduced drug concentration, thus enhanced ocular bioavailability, the method not only provides an enhanced patient compliance, but also avoids the untoward side effects such as blurred vision, irritation, foreign body sensation etc., upon instillation.

In one preferred embodiment, the ophthalmic aqueous solution of difluprednate is useful in the treatment of acute anterior uveitis by twice-a-day instillation into the effected eye of the patient. In another preferred embodiment, the ophthalmic aqueous solution of the present invention is useful in the treatment of chronic uveitis by twice-a-day instillation into the effected eye of the patient.

The inflammatory disorders of the eye that can be treated by administering ophthalmic aqueous solution according to the present invention includes, but are not limited to pain and inflammation associated with ocular surgery, uveitis, acute anterior uveitis, endogenous anterior uveitis, chronic uveitis, inflammation associated with ocular allergies, steroid responsive inflammatory condition of the palpebral and bulber conjunctiva, cornea and anterior segment of the globe such as allergic conjunctivitis, acne rosacea, superficial punctuate keratitis, herpes zoster keratitis. In preferred embodiments, the ophthalmic aqueous solution according to the present invention is useful in the treatment of various forms of uveitis, such as iritis or anterior uveitis, iridocyclitis and choroiditis or chorioretinitis also known as posterior uveitis, acute anterior uveitis, and chronic uveitis.

In one preferred embodiment, the present invention provides a method of treating acute or chronic anterior uveitis by twice-a-day instillation into the effected eye of the patient, an ophthalmic aqueous solution comprising difluprednate at a concentration of about 0.02% to 0.04% weight by volume, wherein the solution is free of oil.

In one embodiment, the present invention provides a method of treating inflammatory disorder of the eye, said method comprising instilling into the eye of the person in need thereof, an aqueous solution of difluprednate comprising therapeutically effective concentration of difluprednate, a crystal growth inhibitor and pharmaceutically acceptable amounts of a solubilizer comprising a mixture of quaternary ammonium compound and polyethoxylated castor oil, in an aqueous vehicle, wherein the solution is free of oil.

In one embodiment, the present invention provides a method of treating inflammatory disorder of the eye, said method comprising administering into the eye of a person in need thereof, an aqueous solution comprising difluprednate as the sole active ingredient at a concentration of about 0.02% to 0.04% weight by volume, wherein the solution is free of oil and wherein the solution is administered twice-a-day, further wherein the aqueous solution comprises a crystal growth inhibitor and pharmaceutically acceptable amounts of a solubilizer comprising a mixture of quaternary ammonium compound and polyethoxylated castor oil. The crystal growth inhibitor is polyvinyl pyrrolidone or its derivative, the inflammatory disorder of the eye is selected from acute anterior uveitis or chronic uveitis.

The ophthalmic aqueous solution of the present invention is capable of enhancing the ocular bioavailability of difluprednate and thus decreasing its frequency of administration. Whereas Durezol®, the marketed emulsion product of difluprednate is instilled four times a day, the aqueous solution of the present invention requires only twice daily instillation to achieve the desired therapeutic effect.

In one embodiment, the present invention thus provides a method of enhancing the ocular bioavailability of difluprednate, said method comprising twice-daily instillation into the eye of a person in need thereof, an ophthalmic aqueous solution of difluprednate.

In one preferred embodiment, the present invention provides a method of enhancing the ocular bioavailability of difluprednate, said method comprising twice-a-day instillation into the eye of a person in need thereof, an ophthalmic solution comprising therapeutically effective concentration of difluprednate, a crystal growth inhibitor and pharmaceutically acceptable amounts of a solubilizer comprising a mixture of quaternary ammonium compound and polyethoxylated castor oil, in an aqueous vehicle.

The ophthalmic aqueous solution of the present invention enhance the ocular bioavailability of difluprednate and reduce the frequency of administration to twice-a-day administration, for achieving the desired anti-inflammatory effect, as against the repeated four times a day administration required for the marketed emulsion product (Durezol®).

While the present invention is disclosed generally above, additional aspects are further discussed and illustrated with reference to the examples below. However, the examples are presented merely to illustrate the invention and should not be considered as limitations thereto.

Example 1-4

The examples describe ophthalmic aqueous solutions of difluprednate according to the present invention.

TABLE 1

Ophthalmic aqueous solutions of difluprednate

| Ingredients | Quantity (% w/v) | | | |
| --- | --- | --- | --- | --- |
| | Example 1 | Example 2 | Example 3 | Example 4 |
| Difluprednate | 0.03 | 0.04 | 0.04 | 0.04 |
| Benzalkonium chloride | 0.02 | 0.02 | 0.02 | 0.025 |
| n-lauroyl sarcosine | 0.02 | 0.02 | 0.02 | 0.03 |
| Polyoxyl 35 castor oil (Cremophor ® EL) | 4.0 | 4.0 | 4.0 | 5.00 |
| Polyvinyl alcohol | 1.4 | 1.4 | 1.4 | 1.40 |
| Carboxy methyl cellulose | — | — | 0.3 | — |
| Glycerine | 2.0 | 2.0 | 2.0 | 1.60 |
| Boric acid | 0.50 | 0.5 | 0.5 | 0.6 |
| Poly hexa methylene biguanide | — | — | — | 0.005 |
| Disodium edetate | 0.05 | 0.05 | 0.05 | 0.05 |
| Sodium acetate | 0.025 | 0.025 | 0.025 | 0.01 |
| Acetic acid | — | — | — | 0.005 |
| Water for Injection | q.s to 100 | q.s to 100 | q.s to 100 | q.s to 100 |

The required quantity of benzalkonium chloride and difluprednate was taken in a container and polyoxyl 35 castor oil (cremophor EL) was added. Difluprednate was solubilized in the above mixture by intermittent sonication and vortexing to form drug preconcentrate.

The required quantity of polyvinyl alcohol was dissolved in water for injection at 70°–80° C. Other ingredients i.e. boric acid, N-lauryl sarcosine, glycerine, disodium edetate, sodium acetate, acetic acid were separately dissolved in a portion of water for injection. This phase was added to polyvinyl alcohol solution with stirring. Drug preconcentrate was added to the above mixture and dissolved by mixing on magnetic stirrer to get a solution (i). In case of example 4, an additional step was followed wherein required quantity of polyhexa methylene biguanide was added to the solution (i). In case of example 3, an additional step was followed wherein carboxymethyl cellulose pre-mixed with a portion of water was added to the solution (i) obtained above, with stirring. Subsequently volume make up was carried out using water for injection. The solution was filtered with 0.2 micron filter. The resulting ophthalmic aqueous solutions of difluprednate (Example 1-4) had a pH of about 5.0-6.0, osmolality of about 300 mOsm/kg and percentage transmittance of about 99%. The viscosity of ophthalmic aqueous solution of Example 1, 2, and 4 was about 4-5 cps, and the viscosity of ophthalmic aqueous solution of Example 3 was about 20 cps.

The physicochemical stability of the formulations was tested upon storage at room temperature (25° C./40% relative humidity) and at 2-8° C. for 6 months. It was found that the solutions of Example 1-4 remained clear and free from particles, crystals or precipitate upon storage. The percentage transmission was greater than 95% upon storage. The assay of difluprednate remained in the range of 95%-105% w/v, the known and unknown impurities did not increased substantially upon storage and the content of impurities remained below the desired specified limit.

Comparative Examples 1-3

This example illustrates comparative non-working examples 1, 2 and 3 (which are devoid of a solubilizer as per invention) and their comparison with working Examples 5 and 6 as per Invention (which contains a solubilizer having a mixture of quarternary ammonium compound and polyethoxylated castor oil). These examples illustrate the surprising effect of use of a mixture of a quarternary ammonium compound and a polyethoxylated castor oil (cremophor), whose combination acts as an efficient solubilizer of difluprednate in aqueous vehicle.

TABLE 2

Effect of mixture of solubilizer versus single solubilizer versus absence of solubilizer:

| Ingredients | Comparative Examples | | | Example of the present invention | | |
|---|---|---|---|---|---|---|
| | 1 | 2 | 3 | 5 | 6 (a) | 6 (b) |
| | Quantity % w/v | | | Quantity % w/v | | |
| Difluprednate | 0.04 | 0.04 | 0.04 | 0.04 | 0.04 | 0.04 |
| Benzalkonium Chloride | — | 0.02 | — | 0.02 | 0.02 | 0.02 |
| N-Lauryl Sarcosine | 0.02 | 0.02 | 0.02 | 0.02 | — | 0.02 |
| Polyethoxylated castor oil (Cremophor ® EL) | — | — | 4.00 | 4.00 | 4.00 | 4.00 |
| Polyvinyl Alcohol | 1.40 | 1.40 | 1.40 | 1.40 | 1.40 | — |
| Polyvinyl Alcohol-PEG graft co-polymer | | | | — | | 3.00 |
| Glycerol | 2.20 | 2.20 | 2.20 | 2.20 | 2.20 | 2.20 |
| Water for Injection | q.s to 100 | | | | | |
| Observation upon storage at room temperature | Immediate Precipitation-clear solution not formed | | Precipitation within 2 day | No precipitation till 6 months (−) | | |
| Time Point at which precipitation observed (+); No precipitation (−) | (+++) | | (+) | | | |

Benzalkonium Chloride is a widely used component as preservative in the ophthalmic formulations. However the inventors found that Benzalkonium chloride plays an important role for the solubilisation and stabilization of difluprednate molecule in aqueous system when used along with a non-ionic surfactant like Cremophor®.

The inventors found that a combination of a quarternary ammonium compound such as benzalkonium chloride and a non-ionic surfactant such as Polyethoxylated castor oil) (Cremophor®), solubilizes the hydrophobic drug—difluprednate in aqueous vehicle and leads to formation of a storage stable clear aqueous solution, (working examples 5 and 6) which solution remains clear and there occurs no precipitation or crystallization of difluprednate upon long term storage (at least 6 months) at room temperature.

The inventors observed that use of a quarternary ammonium compound along with a non-ionic surfactant, Cremophor® is necessarily required for solubilization of difluprednate. It was found that the quarternary ammonium compound along with Cremophor® plays an important role for the solubilisation and stabilization of difluprednate molecule in aqueous system. Only when the two are present together, the drug gets solubilized in aqueous vehicle and there occurs no precipitation upon storage.

However, in absence of either or both of quarternary ammonium compound (like benzalkonium chloride) or Polyethoxylated castor oil (Cremophor®), proper solubilisation of difluprednate in aqueous solution do not take place and the resulting formulations were unstable such that difluprednate gets crystallized out or precipitated out (comparative examples 1-3).

Comparative Examples 4-10

These comparative examples tests the effect of various crystal growth inhibitors on solubilisation and stabilization of difluprednate in aqueous solutions:

Aqueous solutions of difluprednate were prepared by substituting polyvinyl alcohol with other crystal growth inhibitors like hydroxypropyl methylcellulose, hydroxyl ethyl cellulose, hydroxyethyl starch, polyvinylpyrrolidone, carboxyvinyl polymer etc. and physical stability of the solutions was studied upon storage at room temperature. The details of the quantitative formulations tested along with stability study results are presented below in Table 3:

TABLE 3

Effect of crystal growth inhibitors

| Category | Ingredients | Comparative Examples | | | | | | |
|---|---|---|---|---|---|---|---|---|
| | | 4 | 5 | 6 | 7 | 8 | 9 | 10 |
| | | Amount (% w/v) | | | | | | |
| Anti-inflammatory | Difluprednate | 0.04 | | | | | | |
| Solubilizer | Benzalkonium Chloride | 0.02 | | | | | | |
| | Polyethoxylated castor oil (Cremophor ® EL) | 4.00 | | | | | | |
| Preservative | N-Lauryl Sarcosine | 0.02 | | | | | | |
| Co-solvent | Glycerol | 2.20 | | | | | | |
| Excipients tried for their precipitation/ crystal growth inhibition effect | Hydroxypropyl methyl cellulose | 0.2 | | | | | | — |
| | Polyvinylpyrrolidone (Povidone ® K-90) | — | 1.0 | | | | | — |
| | Carboxyvinyl polymer (Carbopol ® 934) | — | | 0.1 | | | | — |
| | Hydroxyethyl starch | — | | | 1 | | | — |
| | Guar gum | — | | | | 0.2 | | — |
| | Polyoxyethylene-polyoxypropylene co-polymer (Pluronic F-68) | — | | | | | 1 | — |
| Vehicle | Water for Injection | q.s. to 100 | | | | | | |
| Observation upon storage at room temperature | | 5 week | within 24 hours | | | 12 days | | |
| Time Point at which precipitation observed (+); | | (+) | (+) | | | (+) | | |

The inventors of the present invention surprisingly discovered that only a particular polymer that is, polyvinyl alcohol or its derivatives, works as efficient crystal growth inhibitor, which maintains proper solubilization of difluprednate in aqueous solution, and prevents crystallization or precipitation of drug upon long term storage at room temperature. (working examples 1-6 of the present invention). On the other hand, when other polymers or surfactants other than polyvinyl alcohol were used, (comparative examples 4-9), it was found that there occurred precipitation or crystallization of drug, at varying time points as given in Table 3.

Example 7

Preservative Efficacy Testing: The formulation of Example 4 was tested for efficacy of antimicrobial preservation, as per the preservative efficacy test specified in the European Pharmacopoeia, 7.0 Edition, section 5.3.1, page 505-506.

The results of Preservative Efficacy Testing for bacteria as per acceptance criteria's A and B specified in the European Pharmacopoeia are presented below in Table 4:

TABLE 4

Results for Preservative Efficacy Testing:

PET Results - European Pharmacopoeia Criteria-A

| Bacteria | Log reduction for compliance | Observation |
|---|---|---|
| Bacteria Log reduction At 6 Hr | | |
| P. Aeruginosa | NLT 2.0 | 5.16 |
| S. Aureus | NLT 2.0 | 5.05 |
| Bacteria Log reduction At 24 Hr | | |
| P. Aeruginosa | NLT 3.0 | 5.16 |
| S. Aureus | NLT 3.0 | 5.05 |
| Bacteria Log reduction At 28 Days | | |
| P. Aeruginosa | No recovery | 5.16 |
| S. Aureus | No recovery | 5.05 |
| Result as per bacteria log reduction | | Complies |

PET Results - European Pharmacopoeia Criteria-B

| Bacteria | Log reduction for compliance | |
|---|---|---|

TABLE 4-continued

Results for Preservative Efficacy Testing:

Bacteria Log reduction At 24 Hr

| | | |
|---|---|---|
| P. Aeruginosa | NLT 1.0 | 5.16 |
| S. Aureus | NLT 1.0 | 5.05 |

Bacteria Log reduction At 7 Day

| | | |
|---|---|---|
| P. Aeruginosa | NLT 3.0 | 5.16 |
| S. Aureus | NLT 3.0 | 5.05 |

Bacteria Log reduction At 28 Days

| | | |
|---|---|---|
| P. Aeruginosa | No increase | 5.16 |
| S. Aureus | No increase | 5.05 |
| Result as per bacteria log reduction | | Complies |

It was observed that the aqueous solution of the present invention (example 4) comply with the specifications as per Acceptance Criteria's A and B of efficacy of antimicrobial preservation test defined in European Pharmacopoeia. i.e. required log reduction for the bacteria at 6 h, 24 h and 7 day as per criteria A and 24 h, 7 day and 28 day as per criteria B was achieved. The test of efficacy of antimicrobial preservation was also performed on another batch of aqueous solution which did not contained a biguanide and it was observed that the efficacy of antimicrobial preservation was inferior to that observed in the batch having a biguanide, inclusion of a biguanide like polyhexamethylene biguanide helps in enhancing the anti-microbial efficacy of the aqueous solution.

Example 8

Animal efficacy study in bovine serum albumin induced chronic uveitis model—Efficacy of difluprednate ophthalmic aqueous solution of the present invention was tested in bovine serum albumin induced chronic uveitis model in NZW rabbits and comparison was made with marketed Durezol® formulation. Various formulations which were tested include:

Placebo, i.e. formulation vehicle similar to Example 1 but not having difluprednate.
Difluprednate ophthalmic aqueous solution of Example 1 having 0.03% w/v of difluprednate.
Difluprednate ophthalmic aqueous solution of Example 2 having 0.04% w/v of difluprednate.
Reference Item, Durezol®—Difluprednate (0.05% w/v) ophthalmic emulsion formulation by Alcon.

The study was performed in NZW rabbits, weighing 3 to 5 kg. The animals were divided into 7 groups, with 5 animals in each group. The 7 groups included—
Group 1—Normal control group
Group 2—Water for injection (WFI) group
Group 3—BSA or bovine serum albumin (disease control) group
Group 4—Placebo group
Group 5—Example 1 group
Group 6—Example 2 group
Group 7—Reference item (Durezol®) group On day 0, all the animals except normal control group were anesthetized with Ketamine and Xylazine by intramuscular route and one drop of lignocaine was applied in each eye for topical anesthesia. On day 0, in group 3 to 8, 200 µL of BSA (5%) was injected intravitreally in both eyes and on day 7 animals were challenged with 2.5 mL of BSA (2%) intravenous injection in marginal ear vein. On day 0, in WFI control group (group 2), 200 µL of sterile WFI was injected intravitreally in the same way mentioned above and on day 7, 2.5 mL of WFI was administered intravenously by marginal ear vein.

The placebo, the example 1 solution, example 2 solution and the reference item were administered after 1 hour of intravenous challenge with BSA on the day 7 to respective group of animals and the administration was subsequently carried out till day 27 of the study. 50 µL of placebo, example 1 solution and example 2 solution were instilled topically two times at 12 hours interval to both eye of respective group of animals using micropipette from day 7 to day 27. 50 µL of reference item was instilled four times at 4 hour interval to the both eye of respective group of animals using micropipette from day 7 to day 27. The normal control, WFI and BSA (disease control) animals remain untreated. On day 14, 21 and 28, each animal was anesthetized using ketamine and Xylazine intramuscular injection. The eyes were examined for clinical grading using Zeiss slit lamp. The clinical evaluation of uveitis included evaluation of Total Clinical Score (on a 0 to 10 point basis as given in Table 5) on Day 14, 21 and 28. The clinical evaluation of uveitis further included evaluation of Total Cell Count and Total Protein in Aqueous Humor on Day 28.

TABLE 5

Clinical signs and grade of Uveitis

| Clinical Signs | Grade of Uveitis (Score) |
|---|---|
| Iris hyperemia | |
| Absent | 0 |
| Mild | 1 |
| Moderate | 2 |
| Severe | 3 |
| Dilation of the iris and conjunctival vessels | |
| Absent | 0 |
| Mild | 1 |
| Moderate | 2 |
| Cell Exudate in anterior chamber | |
| Absent | 0 |
| Mild | 1 |
| Moderate | 2 |
| Severe | 3 |
| Presence of fibrinoid exudation in the pupillary area, with intense flare in the anterior chamber | |
| Absent | 0 |
| Mild | 1 |
| Moderate | 2 |
| Total Maximum Clinical Score | 10 |

Observations: The observations of the Total Clinical Score (0-10) on day 14, 21 and 28; Total Cell Count and Total Protein in Aqueous humor on day 28, are presented below in Table 6:

made with marketed Durezol® formulation. Various formulations which were tested include:

Placebo: Formulation vehicle similar to Example 1 but not having difluprednate.

TABLE 6

Observations

| Groups | Total Clinical Score (0-10) | | | | | | TLC ($10^4$)/ml of aqueous humour | | Total Protein (pg/ml) | |
|---|---|---|---|---|---|---|---|---|---|---|
| | Day 14 | | Day 21 | | Day 28 | | Day 28 | | Day 28 | |
| | Mean | SD | Mean | SD | Mean | SD | Mean | SEM | Mean | SD |
| Normal Control | 1.00 | 0.9 | 0.80 | 1.0 | 1.40 | 1.1 | 0.00 | 0.00 | 1.09 | 1.09 |
| WFI Control | 1.20 | 1.2 | 1.20 | 0.9 | 1.40 | 0.5 | 0.00 | 0.00 | 0.95 | 0.76 |
| BSA (Disease Control) | 5.30 | 2.8 *** | 7.60 | 1.1 *** | 7.80 | 0.8 *** | 10.75 | 3.65 *** | 15.91 | 6.26 *** |
| Placebo | 6.30 | 0.9 ns | 7.70 | 1.6 ns | 8.00 | 0.9 ns | 12.70 | 4.74 ns | 13.53 | 6.11 ns |
| Example 1 group | 4.20 | 0.8 $ | 2.90 | 2.3 $$$ | 3.40 | 2.6 $$$ | 2.85 | 2.77 $$$ | 3.24 | 2.91 $$$ |
| Example 2 group | 5.10 | 1.3 ns | 3.50 | 3.3 $$$ | 3.30 | 2.6 $$$ | 2.15 | 0.97 $$$ | 4.09 | 3.57 $$$ |
| Reference Item-Durezol ® group | 4.70 | 2.5 ns | 3.60 | 2.2 @@@ | 3.30 | 2.0 @@@ | 3.05 | 1.21 @@@ | 4.29 | 4.80 @@@ |

Total clinical score Data were analyzed using Two way ANOVA followed by Bornferroni test
WFI vs BSA (Disease control); ***= p < 0.001, BSA(Disease control) vs Placebo; ns = non-significant, Placebo vs example 1, example 2; ns = non-significant, $ = p < 0.05, $$ = p < 0.01, $$$ = p < 0.001, BSA(Disease control) vs Reference item Durezol ®; ns = non-significant, @@@ = p < 0.001
Total cell count and Total protein: Data were analyzed using One way ANOVA followed by Bornferroni test WFI vs BSA (Disease control); *** = p < 0.001, BSA (Disease control) vs Placebo; ns = non significant, Placebo vs example 1, example 2; ns = non significant; $$$ = p < 0.001, BSA (Disease control) vs Reference item Durezol ®; @@@ = p < 0.001

It was observed that the difluprednate ophthalmic aqueous solution of the present invention having 0.03% w/v-0.04% w/v difluprednate (example 1 and 2) when instilled twice-a-day into the eye effected by chronic uveitis, it showed a significant inhibition in total clinical score, total cell count and total protein as compared to Placebo. Particularly, in case of Example 1 group, wherein the aqueous solution has 0.03% w/v of difluprednate, the mean clinical score reduced significantly from 7.7 (placebo) to 2.9 at day 21 and from 8.0 (placebo) to 3.4 at day 28. Similarly, in case of Example 2 group, wherein the formulation has 0.04% w/v of difluprednate, the mean clinical score reduced significantly from 7.7 (placebo) to 3.5 at day 21 and from 8.0 (placebo) to 3.3 at day 28.

The total clinical score, total cell count and total protein levels were also significantly attenuated by reference item Durezol® as compared to BSA (disease control) group.

The clinical score values, the total cell count and total protein content in aqueous humor observed at day 14, 21 and 28 by twice-a-day administration of low concentration (0.03% and 0.04%) difluprednate ophthalmic aqueous solution of the present invention was equivalent or better than that observed upon four times a day administration of higher concentration 0.05% w/v emulsion formulation Durezol (marketed reference item).

Example 9

Animal efficacy study in lipopolysaccharide (LPS) induced acute uveitis model—Efficacy of Difluprednate ophthalmic aqueous solution of the present invention was tested in lipopolysaccharide (LPS) (an endotoxin) induced acute uveitis in female NZW rabbits and comparison was Difluprednate ophthalmic aqueous solution of Example 1 having 0.03% w/v of difluprednate.
Difluprednate ophthalmic aqueous solution of Example 2 having 0.04% w/v of difluprednate.
Durezol® Difluprednate (0.05% w/v) ophthalmic emulsion formulation by Alcon.

The study was performed in NZW rabbits, weighing 3 to 5 kg. The animals were divided into 7 groups, with 5 animals in each group. The 7 groups included—
Group 1—Normal control group
Group 2—Phosphate buffer saline (PBS) group
Group 3—Lipopolysaccharide (LPS disease control) group
Group 4—Placebo group
Group 5—example 1 group
Group 6—example 2 group
Group 7—Reference item (Durezol®) group.

On day 0, all the animals except normal control group were anesthetized with Ketamine and Xylazine by intramuscular route and one drop of lignocaine was applied in each eye for topical anaesthesia. On day 0, in PBS control group, 20 µL of sterile phosphate buffer saline pH-7.4 was injected intra-vitreally in both eyes. In group 3 to 8, 20 µL of LPS (100 ng) was injected intra-vitreally in both eyes The placebo, the example 1 and 2 solutions and reference item were administered 1 hour after LPS injection, wherein 50 µL of placebo and example 1 and 2 solutions were instilled topically two times at 12 hours interval to both eye of respective group of animals using micropipette, while 50 µL of reference item was instilled four times at 4 hour interval to the both eye of respective group of animals using micropipette. The normal control, PBS and LPS (disease control) animals remain untreated. After 24 hours of LPS injection, each animal was anesthetized using ketamine and Xylazine intramuscular injection. The eyes were examined for clinical grading using Zeiss slit lamp.

The clinical evaluation of uveitis included evaluation of Total Clinical Score (on a 0 to 5 point basis as given in Table 7 below) on Day 1. The clinical evaluation of uveitis further included evaluation of Total Cell Count and Total Protein in aqueous humor on Day 1. Aqueous humor was collected from each animal using 30 gauge needle attached with appropriate syringe after clinical scoring. Aqueous humor samples were stored at 2-8° C. till analysis. The total cell count and total protein of each animal were calculated.

TABLE 7

Clinical signs and grade of Uveitis

| Clinical Signs | Grade of Uveitis (Score) |
|---|---|
| Iris hyperemia | |
| Absent | 0 |
| Mild | 1 |
| Moderate | 2 |
| Severe | 3 |
| Pupil | |
| Normal | 0 |
| After Miosis | 1 |
| Exudate in anterior chamber | |
| Absent | 0 |
| Present | 1 |
| Total Maximum Clinical Score | 5 |

Observations: The observations of the Total Clinical Score (0-5); Total Cell Count and Total Protein in aqueous humor on day 1, are presented below in Table 8:

TABLE 8

Observations

| Groups | Total Clinical Score (0-5) | | TLC ($10^4$)/ml of aqueous humour | | Total Protein (pg/ml) | |
|---|---|---|---|---|---|---|
| | Mean | SD | Mean | SEM | Mean | SD |
| Normal Control | 0.0 | 0.0 | 0.15 | 0.1 | 0.91 | 0.6 |
| PBS Control | 0.3 | 0.5 | 0.15 | 0.1 | 1.04 | 0.3 |
| LPS (Disease Control) | 3.1 | 0.7 ### | 231.75 | 87.4 # | 21.94 | 4.7 ### |
| Placebo | 3.0 | 1.1 ns | 224.8 | 71.4 Ns | 20.23 | 3.9 Ns |
| Example 1 | 1.0 | 0.9 $$$ | 30.2 | 12.9 $ | 9.65 | 8.8 $ |
| Example 2 | 0.7 | 0.8 $$$ | 29.56 | 18.6 $ | 10.11 | 9.1 $ |
| Durezol ® | 0.7 | 0.5 *** | 21.2 | 9.8 * | 13.21 | 8.6 * |

Total clinical score:
PBS vs LPS (Disease control) = t-test (# = p < 0.05, ### = p < 0.001),
LPS (Disease control) vs Placebo = t-test; (ns=non significant);
Placebo vs example 1 and 2 = One way ANOVA followed by Dunnett's Multiple Comparison Test ($ = p < 0.05, $$ = p < 0.01, $$$ = p < 0.001),; LPS (Disease control) vs Reference Durezol = t-test (* = p < 0.05,  = p < 0.01, * = p < 0.001); Durezol vs example 1, example 2 = One way ANOVA followed by Dunnett's Multiple Comparison Test ($ = p < 0.05, ns = non-significant)

It was observed that the difluprednate ophthalmic aqueous solution of the present invention having 0.03% w/v-0.04% w/v difluprednate (example 1 and 2) when instilled twice-a-day into the eye effected by acute uveitis, it showed a significant inhibition in total clinical score, total cell count and total protein as compared to Placebo. Particularly, in case of example 1 group, (0.03% w/v difluprednate solution), the mean clinical score reduced significantly from 3.0 (placebo) to 1.0 at day 1. Similarly, in case of example 2 group, (0.04% w/v difluprednate solution), the mean clinical score reduced significantly from 3.0 (placebo) to 0.7.

The total clinical score, total cell count and total protein levels were also significantly attenuated by reference item Durezol® as compared to BSA (disease control) group. Particularly, the mean clinical score reduced from 3.0 (placebo) to 0.7 at day 1.

The clinical score values, the total cell count and total protein content in aqueous humor observed at day 1 by twice-a-day administration of low concentration (0.03% w/v and 0.04% w/v) difluprednate ophthalmic aqueous solution of the present invention was equivalent or better than that observed upon four times a day administration of higher strength 0.05% w/v emulsion formulation Durezol® (marketed reference item).

The invention claimed is:

1. A clear ophthalmic aqueous solution comprising:
   a. about 0.02% w/v to about 0.04% w/v difluprednate,
   b. about 0.5% w/v to about 3.0% w/v of a crystal growth inhibitor, and
   c. a solubilizer comprising a mixture of:
      i. about 0.01% w/v to about 0.05% w/v quaternary ammonium compound and
      ii. about 1.5% w/v to about 6.0% w/v polyethoxylated castor oil,
   in an aqueous vehicle;
   wherein the crystal growth inhibitor is polyvinyl alcohol or derivative thereof, wherein the difluprednate is not in microparticulate form.

2. The clear ophthalmic aqueous solution according to claim 1, wherein the therapeutically effective concentration of difluprednate is about 0.03% w/v to 0.04% w/v.

3. The clear ophthalmic aqueous solution according to claim 1, wherein the quaternary ammonium compound is benzalkonium chloride.

4. The clear ophthalmic aqueous solution according to claim 1, wherein the polyethoxylated castor oil is about 3.0% w/v to about 5.0% w/v.

5. The clear ophthalmic aqueous solution according to claim 4, wherein the polyethoxylated castor oil is polyoxyl 35 castor oil.

6. The clear ophthalmic aqueous solution according to claim 1, wherein the polyvinyl alcohol or derivative thereof is about 1.4% w/v.

7. The clear ophthalmic aqueous solution according to claim 1, wherein the solution further comprises a preservative selected from the group consisting of biguanide, boric acid, n-lauryl sarcosine and mixtures thereof.

8. The clear ophthalmic aqueous solution according to claim 2, wherein the solution is administered into the eye of a person in need thereof twice a day.

9. The clear ophthalmic aqueous solution according to claim 1, wherein the solution percent transmission of the solution is more than 90%.

10. The clear ophthalmic aqueous solution according to claim 2, wherein the difluprednate is 0.04% w/v.

11. The clear ophthalmic aqueous solution according to claim 1, wherein the difluprednate is 0.03% w/v.

12. The clear ophthalmic aqueous solution according to claim 1, wherein the polyvinyl alcohol or derivative thereof is about 3.0% w/v.

13. The clear ophthalmic aqueous solution according to claim 1, wherein the quaternary ammonium compound is about 0.025% w/v.

14. The clear ophthalmic aqueous solution according to claim 1, wherein the polyethoxylated castor oil is about 5.0% w/v.

15. A clear ophthalmic aqueous solution comprising:
   a. about 0.03% w/v to about 0.04% w/v difluprednate,
   b. about 0.5% w/v to about 3.0% w/v polyvinyl alcohol or derivative thereof,
   c. about 0.01% w/v to about 0.05% w/v benzalkonium chloride; and
   d. about 1.5% w/v to about 6.0% w/v polyoxyl 35 castor oil.

* * * * *

UNITED STATES PATENT AND TRADEMARK OFFICE
CERTIFICATE OF CORRECTION

PATENT NO. : 11,000,475 B2  
APPLICATION NO. : 15/768285  
DATED : May 11, 2021  
INVENTOR(S) : Ajay Jaysingh Khopade et al.

Page 1 of 1

It is certified that error appears in the above-identified patent and that said Letters Patent is hereby corrected as shown below:

In the Claims

Column 20, Lines 34-35 (Claim 2): the phrase "therapeutically effective concentration of" should be deleted.

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*